US010166404B2

(12) United States Patent
Gemmel et al.

(10) Patent No.: US 10,166,404 B2
(45) Date of Patent: Jan. 1, 2019

(54) METHOD FOR IRRADIATION PLANNING (71) Applicant: GSI Helmholtzzentrum Fur Schwerionenforschung GmbH, Darmstadt (DE)

(72) Inventors: Alexander Gemmel, Erlangen (DE); Christoph Bert, Uttenreuth (DE)

(73) Assignee: GSI Helmholtzzentrum fur Schwerionenforschung GmbH, Darmstadt (DE)

( * ) Notice: Subject to any disclaimer, the term of this patent is extended or adjusted under 35 U.S.C. 154(b) by 251 days.

(21) Appl. No.: 14/442,255

(22) PCT Filed: Oct. 30, 2013

(86) PCT No.: PCT/EP2013/072690
§ 371 (c)(1),
(2) Date: May 12, 2015

(87) PCT Pub. No.: WO2014/072213
PCT Pub. Date: May 15, 2014

(65) Prior Publication Data
US 2016/0271422 A1 Sep. 22, 2016

(30) Foreign Application Priority Data
Nov. 12, 2012 (DE) .................. 10 2012 110 864

(51) Int. Cl.
*A61N 5/10* (2006.01)
(52) U.S. Cl.
CPC ........... *A61N 5/103* (2013.01); *A61N 5/1037* (2013.01); *A61N 5/1048* (2013.01); *A61N 5/1038* (2013.01); *A61N 2005/1087* (2013.01)

(58) Field of Classification Search
USPC ...................................... 250/492.1
See application file for complete search history.

(56) References Cited

U.S. PATENT DOCUMENTS 7,616,735 B2* 11/2009 Maciunas ............. A61N 5/103
378/65
8,217,373 B2* 7/2012 Bert ....................... A61N 5/103
250/252.1
(Continued)

FOREIGN PATENT DOCUMENTS

CN 101940066 A 1/2011
CN 102089034 A 6/2011
(Continued)

OTHER PUBLICATIONS

Chinese Office Action, Application No. 201380069777.7, Applicant: GSI Helmholtzzentrum Fuer Schwerionenforschung GmbH, dated Jun. 24, 2016.
(Continued)

*Primary Examiner* — Phillip A Johnston
(74) *Attorney, Agent, or Firm* — Reising Ethington PC (57) ABSTRACT

Method for irradiation planning of a target volume with a scanned particle beam, comprising the following steps: defining a target volume located in a body, subdividing the target volume into a plurality of individually approachable target points, defining a number of temporally consecutive irradiation sub-plans, dividing the target points of the target volume among the irradiation sub-plans in subsets, wherein the subsets are distributed over the entire target volume, and wherein mutually adjacent target points of the target volume are each assigned to different irradiation sub-plans.

34 Claims, 10 Drawing Sheets (56) References Cited

U.S. PATENT DOCUMENTS

| | | | |
|---|---|---|---|
| 8,405,050 B2* | 3/2013 | Bert | A61N 5/103 250/491.1 |
| 8,504,188 B2 | 8/2013 | Keibel | |
| 8,644,571 B1* | 2/2014 | Schulte | A61N 5/1039 250/307 |
| 9,511,241 B2* | 12/2016 | Chen | A61N 5/103 |
| 2009/0022264 A1 | 1/2009 | Zhou et al. | |
| 2010/0104068 A1 | 4/2010 | Kilby et al. | |
| 2011/0280372 A1 | 11/2011 | Ivanov | |
| 2011/0297849 A1 | 12/2011 | Bert et al. | |
| 2011/0303858 A1 | 12/2011 | Bert et al. | |
| 2012/0187314 A1 | 7/2012 | Bert et al. | |

FOREIGN PATENT DOCUMENTS

| | | |
|---|---|---|
| CN | 102223913 A | 10/2011 |
| CN | 102548613 A | 7/2012 |
| DE | 102008027485 | 12/2009 |
| DE | 102009033297 | 1/2011 |
| EP | 2197251 A1 | 6/2010 |
| JP | 2005050823 A | 2/2005 |
| JP | 2006087649 A | 4/2006 |
| JP | 2008136523 A | 6/2008 |
| JP | 2012506724 A | 3/2012 |
| WO | 2010043340 | 4/2010 |

OTHER PUBLICATIONS

English translation of the International Preliminary Examination Report, Int. Serial No. PCT/EP2013/072690, Int. Filing Date: Oct. 30, 2013, Applicant: GSI Helmholtzzentrum Fur Schwerionenforschung GmbH, dated May 12, 2015.

JP Office Action, Patent Application No. 2015-541081, dated Feb. 3, 2016, Applicant: Yuzuru Okabe, et al.

International Search Report and Written Opinion, Int. Serial No. PCT/EP2013/072690, Int. Filing Date: Oct. 30, 2013, Applicant: GSI Helmholtzzentrum Fur Schwerionenforschung GmbH, dated Mar. 4, 2014.

German Office Action, Serial No. 10 2012 110 864.1, Applicant: GSI Helmholtzzentrum Fur Schwerionenforschung GmbH, dated Sep. 16, 2013.

* cited by examiner

METHOD FOR IRRADIATION PLANNING

TECHNICAL FIELD

The present disclosure concerns a method and a device for irradiation planning, as well as an accelerator device with a particle beam.

BACKGROUND

Tumor therapy with heavy ions has come to be an established method for treating tissue, for example, tumor diseases, over the course of recent decades. However, the experience gained thereby is also applied in purely technical areas.

A common feature of all known methods is that a focused particle beam provided by an accelerator is conducted to one or more radiation or treatment rooms by means of a high energy beam transport system. In the radiation room, a target volume to be irradiated is positioned, and irradiated with the particle beam.

It is known that a target volume to be irradiated can move. For example, a lung tumor which moves as the patient breathes may be located in the target volume. For the purpose of investigating the effect the motion has on the treatment success of the particle therapy, however, the motion can also be simulated by means of non-living model bodies referred to as phantoms.

It is a particular challenge in the context of particle therapy to achieve the most homogeneous distribution possible of the radiation dose deposited in the tissue. One reason for which homogeneous dose distribution in the target volume is of particular interest is the fact that the cells of the tumor located in the target volume only die with adequate reliability at or above a threshold dose, while at the same time, excessive radiation burden to the surrounding healthy tissue should be avoided. Thus, in irradiation methods in which a plurality of individual radiation doses are to be successively deposited in various target points in the target volume, which is to say with a scanned particle beam, it is still difficult to achieve this desired homogeneous dose distribution in the target volume if the target volume moves during radiation. Improvement of the homogeneity of dose distribution in target volumes thus remains the subject of current research.

For example, in the case of a scanned particle beam, one possibility is to distribute the radiation dose to be applied over several passes, which is called "rescanning." In this method, the target points of the target volume are approached multiple times so that the total dose to be applied is built up successively by multiple individual doses applied repeatedly during the rescanning passes. Repeatedly approaching the target points with individual doses allows for a statistical averaging over the individual doses, by which means any incorrectly deposited doses can be averaged, statistically speaking. Motions of the target volume can be at least partly compensated for in this way.

Nevertheless, in this process each target point is approached multiple times with an appropriately reduced sub-dose, which can cause radiation by rescanning to take a substantial additional amount of time, since the extraction rate must be reduced in accordance with the reduced sub-dose. It is the state of the art that it is necessary to put up with a prolonged radiation process in order to increase the homogeneity of the dose distribution and thus, in the case of radiotherapy, to improve the treatment success.

In addition, it is known to track the motion of the target volume and to take this into account in calculating the individual doses.

GENERAL DESCRIPTION

Therefore, the object of the present disclosure is to provide a method that simplifies irradiation planning for a target volume, and that in doing so diminishes or eliminates one or more of the aforementioned disadvantages of the prior art.

It is also desirable for the present disclosure to reduce the time required for the full treatment or dose application.

Another object of the present disclosure is to make the radiation result more robust to changes, for example, motions, of the target volume.

The object of the present disclosure is attained by the subject matter of the independent claims. Advantageous enhancements of the present disclosure are defined in the dependent claims.

Irradiation planning for a target volume located in a body, which process creates the irradiation plan step by step, is defined according to the present disclosure using the following steps:

First, a target volume is defined, which typically is located in a body. The target volume in this context can be located in a non-living body such as, e.g., a material sample, a phantom, or a test setup, or else can comprise living material such as, e.g., cell samples or experimental animals. For example, tumor cells are located in the target volume. The target volume is subdivided into a plurality of individually approachable target points. In other words, a raster of target points with defined point spacing is placed in the target volume.

Then a nominal dose, which is to say the planned or desired value of the radiation dose to be deposited in the applicable target point, is associated with each of the target points. In other words, the nominal dose is written on the applicable target points in the irradiation plan. Incidentally, many of the terms used in this application, for example target volume, target point, nominal dose, dose distribution, etc., are defined in the ICRU Report 50 (with the Addendum Report 62), which has been accepted as a guideline.

Next, the irradiation plan is divided into a number of temporally consecutive irradiation sub-plans. This means that the irradiation plan specifies executing the irradiation sub-plans one after the other in direct succession.

The target points of the target volume are divided among the irradiation sub-plans in subsets, wherein the subsets are distributed over the entire target volume. Target points that are adjacent to one another are assigned to different irradiation sub-plans. In other words, each subset comprises target points that are distributed over the entire target volume and are not directly adjacent to one another.

The two first-mentioned steps correspond to the prior art method for dividing up a target volume.

Until now in the prior art, the target points of the target volume typically are approached successively, which is to say one after the other, in this context. This method has become established because it is especially easy to carry out.

The target points can be assigned to iso-energy layers, making it possible to irradiate an iso-energy layer with constant particle energy, which is to say, for example, unchanged accelerator settings.

In the method according to the present disclosure, the irradiation plan is divided into temporally consecutive irradiation sub-plans.

Mutually adjacent target points of the target volume are assigned to different irradiation sub-plans. When the irradiation sub-plans are executed consecutively, then target points that are adjacent to one another are not irradiated consecutively in time, but instead the first target point is irradiated in a first irradiation sub-plan, and the target points adjacent to the first target point are irradiated in at least one other irradiation sub-plan. This can increase the robustness of the dose deposition with regard to motions of the target volume. In other words, the dose position at the particular target points can be improved by the means that mutually adjacent target points are approached with a time delay rather than one directly after the other. Due to the division of mutually adjacent target points among different irradiation sub-plans, therefore, the homogeneity of the dose distribution can also be increased. In some circumstances, moreover, it can suffice to approach a target point just one single time with this method, making it possible to realize substantial time savings. This means that, under certain circumstances, no rescanning at all is performed with the method according to the present disclosure. The possibility is not precluded, however, of combining the method according to the present disclosure with rescanning, depending on the requisite target dose distribution, in order to obtain the best possible result in each case.

As a result of the fact that the subsets of the target points of the irradiation sub-plans are distributed over the entire target volume, the entire target volume is already covered by each of the irradiation sub-plans. In other words, a coarse raster of a dose distribution is deposited in the target volume with the first irradiation sub-plan, and the homogeneity of the dose distribution is refined with each subsequent irradiation sub-plan, since in each case subsets of target points are approached that are adjacent to the preceding subsets. For example, the subsets of target points are proper subsets in the mathematical sense, which is to say they are partial sets of the total set of target points, none of which includes the full number of target points.

If an unanticipated or incorrectly calculated motion of the target volume later takes place during the application of the dose to one of the target points of one of the irradiation sub-plans, as a result of which the dose to be applied is not deposited in the target point but rather is deposited incorrectly, then this can be compensated for statistically, at least in part, by the preceding or subsequent irradiation sub-plans.

In each individual irradiation process, wherein an individual dose is applied to a target point, the entire entry path of the particle beam receives a dose amount referred as the pre-dose. In a resource-intensive irradiation planning method, all pre-doses that arise must be taken into account and used to calculate the total dose. Thus, it is possible, for example, to first irradiate the distal end of a target volume, in which process the more proximal part of the target volume is already subjected to a pre-dose. The target volume can then be irradiated from the opposite end, for example, so that the part of the target volume that is distal from this end receives an additional sub-dose. In the ideal case, the dose distribution over the target volume corresponds to a step function. This is, by its nature, achievable only with difficulty in practice.

The target points can be assigned to the subsets in spatial alternation. This means that a first target point is assigned to the first subset, and a second target point can be assigned to the second subset. For example, the target points are assigned to the subsets in spatial alternation in two directions transverse to the beam axis, which is to say laterally, and/or in spatial alternation in three dimensions. The number of irradiation sub-plans also determines the number of target point subsets in this context.

Consequently, the target points of the subsets preferably are contiguously surrounded by only target points that are assigned to different subsets. The target points preferably can be assigned to the different irradiation sub-plans in alternation within rows and/or columns in checker-board style. For example, target points in a first row or column can be placed in the first and second subsets, and target points in a second row or column can be placed in the third and fourth subsets, in a checkerboard-like fashion. In this case, only two "colors" of the checker-board pattern should be considered for the checkerboard-like structure, under the premise that the subsets assigned to the colors alternate in even or odd rows or columns in each case.

The number of irradiation sub-plans can correspond to the number of "colors" of the checkerboard in this analogy, and this can mean a multi-colored checkerboard pattern; For example, in the three-dimensional case, the target points are then assigned to the different irradiation sub-plans in checkerboard-like alternation, wherein one square (in the checkerboard analogy) is always adjoined by squares of different colors.

When the target points of the irradiation sub-plans are approached by the scanned beam of the particle facility, adjacent target points of the target volume within the irradiation sub-plans preferably are skipped. This means that the first target point is approached, but in contrast the spatially adjacent target point of the target volume is skipped. The third target point of the iso-energy layer or of the target volume can then again be a target point of the first irradiation sub-plan, and thus be approached. For example, when the target points of each of the irradiation sub-plans are approached, adjacent target points of the target volume are skipped. In other words, the target points of the irradiation sub-plans are approached in such a way that adjacent target points of the target volume do not follow one another directly.

The target points of at least two subsets can be approached interlaced with one another in a meander pattern in the target volume.

For example, the subsets of the target points do not intersect one another. In other words, the target points are each approached just one single time.

In one preferred embodiment of the present disclosure, a target area of the target volume extends over multiple target points of the target area, wherein the target area corresponds to the anticipated beam diameter of the scanned beam. The target points in a target area are referred to as a group of target points, or simply group. In other words, one shot of the scanned beam covers multiple target points so that one dose can be deposited in the target points of the target area by each shot of the scanned beam. The target points of the target areas preferably are each assigned to different subsets, so that the target points similarly divide the target area among the different irradiation sub-plans. By covering a target area by multiple irradiation sub-plans, the applicable target area can be approached by at least some of the irradiation sub-plans despite a motion of the target volume. This ensures a certain statistical averaging, and hence a more uniform dose distribution in a moving target volume.

The number of target points in a target area can correspond to the number of irradiation sub-plans. In other words, the number of irradiation sub-plans is a result of how many target points are located in a target area. The target points of the target area are assigned to different subsets here. Ideally, each target area is supplied by each irradiation sub-plan in this context. In other words, of the target points located in a common target area, a maximum of one target point is approached by each irradiation sub-plan. However, it should not be ruled out in this context that, in complex target volume shapes that may be tightly surrounded by at-risk areas (OAR, Organs at Risk), irradiation sub-plans are possible in which at least one target point of a target area is approached, wherein these irradiation sub-plans are proper subsets of the set of target points in the target volume.

If the target points are combined into iso-energy layers and if portions of the target points of the subsets are located in one iso-energy layer, then it is appropriate to approach these portions of the target points consecutively. In other words, each iso-energy layer includes target points from multiple subsets or all subsets. In this way, the target points of the irradiation plan that are located in one iso-energy layer can be approached without changing the accelerator settings under certain circumstances.

For example, the subsets of target points combined into an iso-energy layer can be approached in alternation in rows and columns. In other words, the target points from at least two of the subsets in the iso-energy layers are approached in alternation by rows and columns. In this context, every other row or every other column of target points of an iso-energy layer can be skipped. This is not meant to preclude that it is also possible with the method according to the present disclosure to skip, e.g., every fourth or every sixth row or column of target points of an iso-energy layer, but it is appropriate to skip every other row or every other column of target points of an iso-energy layer.

The irradiation plan has at least four irradiation sub-plans. In this case, one target area accordingly comprises at least four target points that are assigned to different irradiation sub-plans. The spacing between the iso-energy layers, which is to say the spacing of the target points in the beam direction, is preferably chosen here such that the target points of a target area are located in one iso-energy layer. In other words, target points of adjacent iso-energy layers are affected only slightly when the target points of the iso-energy layer are approached.

The number of target points per target area can be adjusted by the means that either the beam diameter is varied or the point spacing between target points is varied. Depending on the motion to be expected, therefore, a target area can have a different number of target points. Consequently, it should not be ruled out that some target areas are not approached by some irradiation sub-plans, since the target area does not have a sufficiently large number of target points on account of the raster. The target points of the target area are then simply divided up among as many irradiation sub-plans as possible so that the effect of statistical averaging occurs here as well. It is also a possibility to include target points simultaneously in different subsets that then partially overlap, so that these target points are approached multiple times and the target areas are covered with each irradiation sub-plan.

In a variation of the raster spacing, the pre-dose can also be taken into account by the means that the point spacing is varied over the target volume, which is to say does not represent a constant quantity over the target volume. In this way, the raster can, if applicable, be adjusted such that each target area is indeed covered by each irradiation sub-plan without target points being approached multiple times.

When the number of irradiation sub-plans is being defined, it is also possible to take into account the number of target areas, the local motion parameters, and/or the pre-dose that arises when other target points are being approached. Thus, in the case of a uniform motion in which no fluctuations are anticipated, a small number of irradiation sub-plans may suffice. In the case of a complex motion that is difficult to predict, it may make sense to specify a larger number of irradiation sub-plans. The larger number of irradiation sub-plans can be achieved here by means of a finer raster of points, which is to say by a smaller spacing between the target points.

Within the scope of the present disclosure, a control device is also provided that can execute the steps of the above-mentioned method.

The present disclosure is explained in detail below using exemplary embodiments and with reference to the figures, wherein identical and similar elements are in part labeled with identical reference numbers, and the features of the various exemplary embodiments can be combined with one another.

BRIEF DESCRIPTION OF THE FIGURES

Shown are:
FIG. 1 an overview of the configuration of a typical radiation facility,
FIG. 2 a schematic representation of components used to control a radiation facility,
FIG. 3 a schematic representation of a deflection and modulation device and an irradiation with active motion compensation,
FIG. 4 the overall irradiation plan of an iso-energy layer,
FIG. 5 the overall irradiation plan of an iso-energy layer wherein the target points are subdivided into A, B, C, and D,
FIG. 6 a irradiation sub-plan as a subset of the overall irradiation plan from FIG. 4, comprising the A points,
FIG. 7 the irradiation sub-plan comprising the B points,
FIG. 8 the irradiation sub-plan comprising the C points,
FIG. 9 the irradiation sub-plan comprising the D points,
FIG. 10 an overview of executable steps of the irradiation planning method in the variants of FIG. 10a, FIG. 10b, and FIG. 10c.

DETAILED DESCRIPTION OF THE FIGURES

Figure 1:
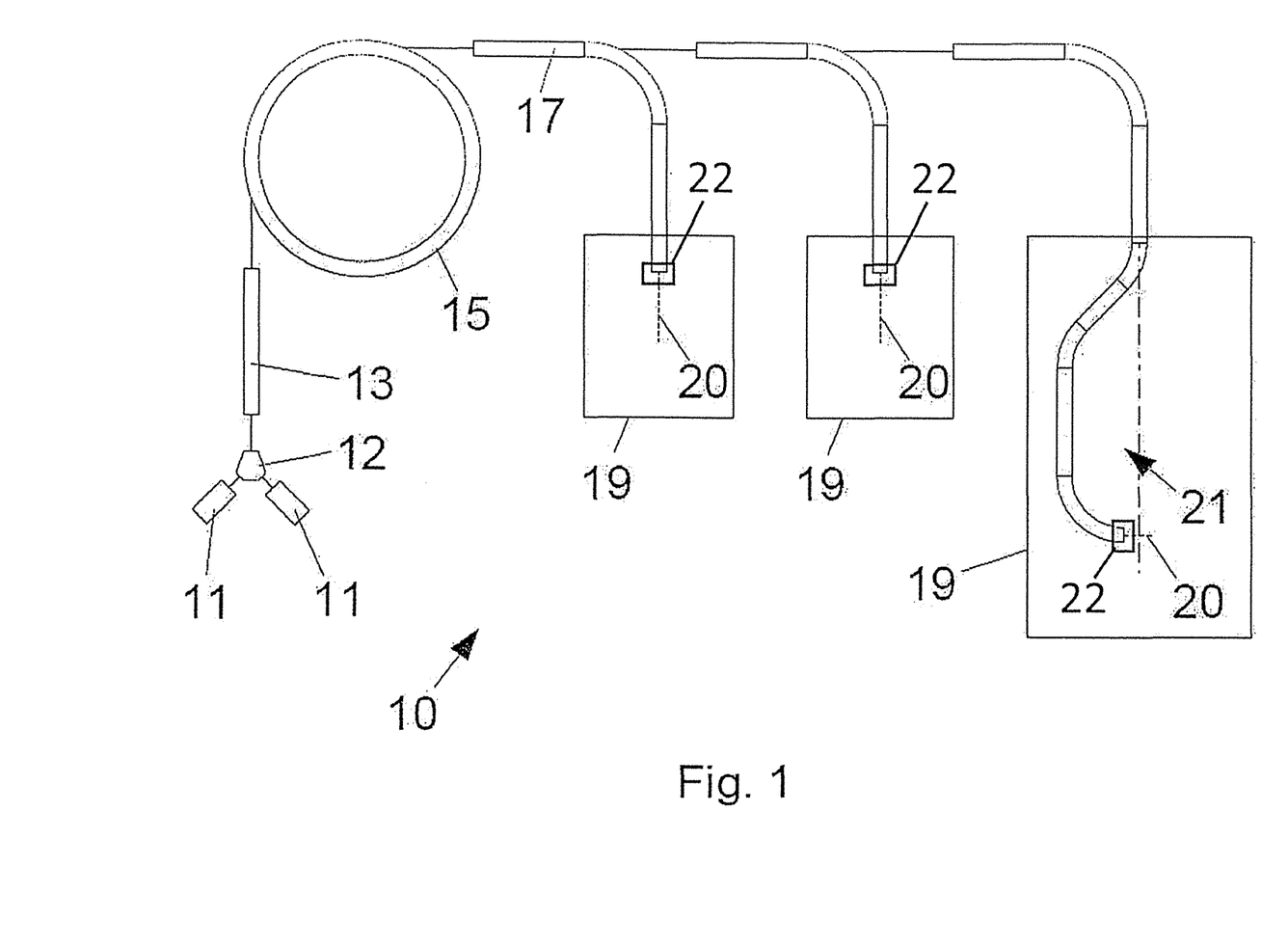

FIG. 1 shows the schematic configuration of a particle therapy facility 10 that is known per se. The particle therapy facility 10 generates and accelerates charged particles that are provided for further use in the form of a particle beam 20 and can be directed by means of a beam guide 17 into a defined target volume 34 (see FIG. 3). The target volume 34 contains a tumor within the framework of tumor therapy, for example, but a target volume 34 that contains nonliving material and/or cell cultures may also be defined for scientific purposes, animal experiments, model and material samples, and in general for investigating the particle beam and/or particle therapy. The particle therapy facility 10 is also used for irradiating phantoms with the particle beam 20, by which means a plurality of radiation parameters can be verified before and/or after a completed irradiation or treatment of a patient.

In the example shown in FIG. 1, the particles are generated and pre-accelerated in one of the two ion sources 11. The ion sources 11 can generate, for example, an extremely wide variety of particles from protons to uranium; protons, pions, helium ions, or especially preferred carbon ions are used because of their properties for particle therapy, such as the characteristic (particle-dependent) interaction with material and the penetration depth. Speaking very generally, hadrons are preferred for use as particles. By means of a low energy beam transfer line 12, the particles are threaded into a pre-accelerator 13, which in the case shown is a linear accelerator 13. The linear accelerator 13 accelerates the particles to a first energy level, and focuses the particles into a particle beam 20. At the first energy level, the particles are ultimately threaded into the accelerator unit 15, for example, a synchrotron as shown here, but also a cyclotron, with another low energy beam transfer line 12, where they are further accelerated up to the extraction energy, which can be set for the application in question. Finally, the beam guide 17 guides the particle beam 20 to the desired target in a measurement room 19 or therapy room 21, where the particle beam 20, with a typical beam diameter of 3 to 30 millimeters, can be applied or is made available.

For precise positioning of the particle beam 20 in order to approach a target point 30 of a target volume 34 in a body 77, a deflection and modulation device 22 for lateral, which is to say horizontal and vertical, deflection of the particle beam 20 and for energy modulation to rapidly vary the particle beam energy, which determines the penetration depth of the particle beam 20, is located in the measurement or radiation room 19 or therapy room 21. Since an entire raster of target points in a target volume can be approached successively by this means, and the successive approach of the target points is called "scanning," the device is referred to as raster scanning device 22.

Speaking very generally, the irradiation methods of spot scanning, continuous radiation, and raster scanning can be used.

The order in which the target points 30 of the target volume 34 are approached is set forth in a irradiation plan, which also can contain additional parameters, for example, such as the parameters of the target volume 34 and/or a motion to be anticipated of the target volume 34. The raster scanning device 22 provides the opportunity to direct the particle beam 20 continuously at the target volume 34.

The entire particle therapy facility 10 is ultimately controlled by an accelerator control system that, for example, controls the accelerator unit 15 and the beam guide 17, and collects measurement data for monitoring beam parameters. If appropriate, the parameters for controlling the particle therapy facility 10 can be set based on the irradiation plan, so that the irradiation plan also includes the setting data for controlling the particle therapy facility 10.

Figure 2:
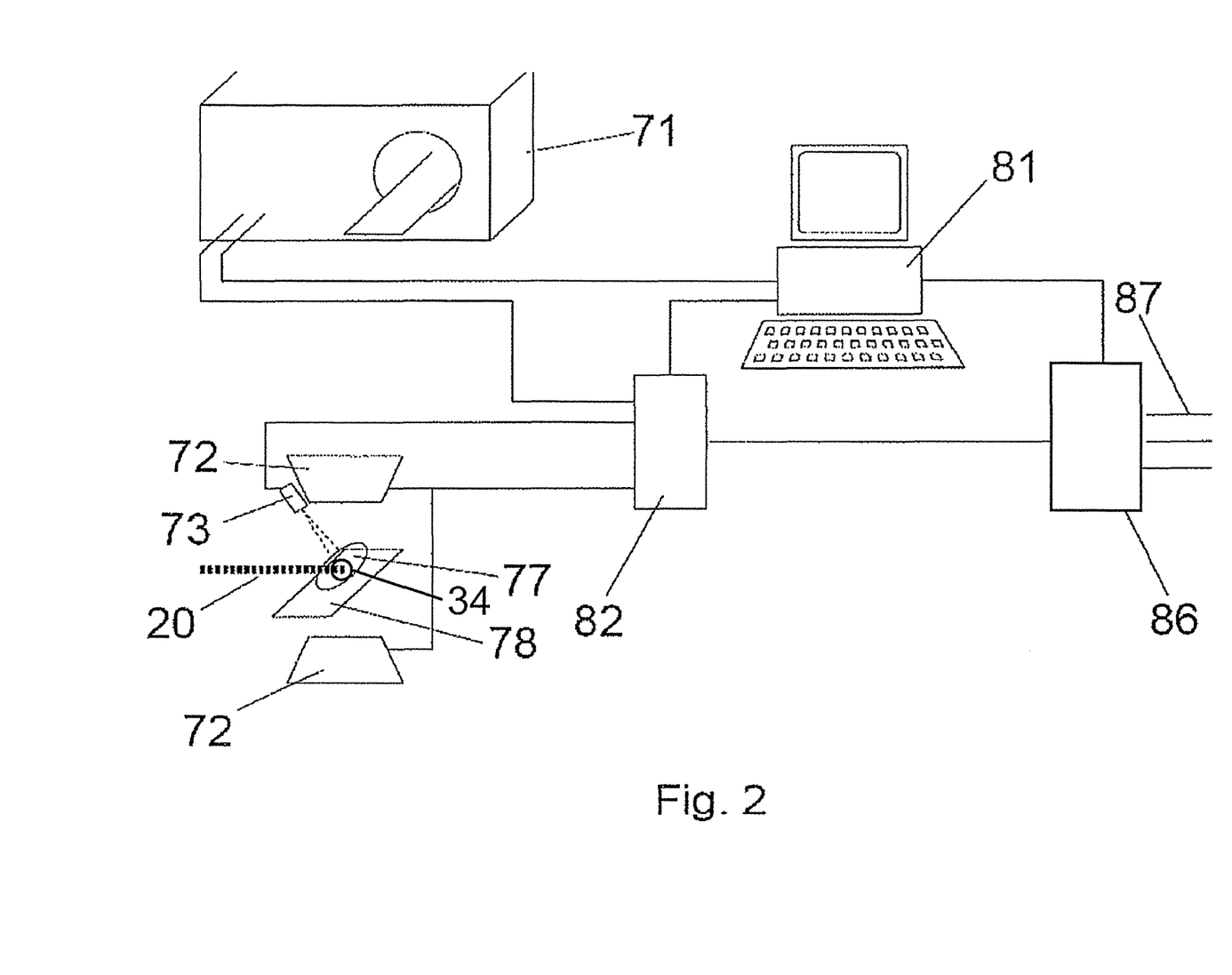

FIG. 2 shows a schematic representation of devices and equipment that are known per se and which can be used in creating a irradiation plan, which is to say in irradiation planning, for creating a data set that defines target points 30 in a target volume 34 in a body 77, and in the control of a particle therapy facility 10 such as was described with reference to FIG. 1, for example.

The position and extent of a tumor to be irradiated or of another target volume 34 can be ascertained by means of a CAT or MRI system 71, or by means of other diagnostic equipment.

Data from the tomography system 71 are processed in a device 81 for creating a data set, either directly or after preparation by additional equipment not shown in FIG. 2. The device 81 is a workstation, a terminal, or other computer, for example. Due to its user interface, software or other features, the device 81 is optionally also suitable for medical staff to use for defining the target volume 34, the doses to be applied, the division of the same into multiple fractions, the direction of the radiation and other details of the particle therapy.

The body 77 to be irradiated can be monitored using variously implemented monitoring equipment before, during or after the irradiation by the particle therapy facility 10. Provided by way of example are a PET camera 72 (PET=positron emission tomography) and/or a distance sensor 73 for sensing a body 77 to be irradiated that is supported on a support surface 78. The PET camera 72 and/or the distance sensor 73 and the support surface 78 can be located within one of the radiation rooms 19 described above with reference to FIG. 1. In this case, the dose produced through a particle beam 20 and motions of the irradiated body 77 can be sensed by means of the PET camera 72 and/or the distance sensor 73. Alternatively, the PET camera 72, the distance sensor 73, and the support surface 78 are located outside of a radiation room. Alternatively or in addition, the body 77 can be monitored by means of a fluoroscopy device, an X-ray device, an ultrasound sensor, a respiration monitoring belt, and/or other external sensors.

Data from the tomography system 71, from the PET camera 72, and from the distance sensor 73 can be processed by a device 82 for determining one or more motion parameters. By means of the device 82, motions of sub-areas of the body 77 (for example because of breathing or heartbeats) can be quantitatively sensed before an irradiation or during an irradiation. The motion parameter or parameters determined by the device 82 can be taken into account by the device 81 for creating a data set.

Especially suitable for being taken into account during the creation of a data set are data regarding the amplitudes of typical and/or periodic motions or regarding a relationship between the spatial position of the target volume and/or a quantity that can be sensed from outside, for example by means of the distance sensor 73. Alternatively or in addition, parameters determined by the device 82 or data can be processed directly by a controller 86 for controlling a radiation facility 10 such as was described with reference to FIG. 1. Data sensed by the PET camera 72 or the distance sensor 73 during the irradiation are especially suitable for this purpose. The data set created by the device 81 is also incorporated into the control of the facility 10 by the control unit 86. The control unit 86 is linked to the radiation facility 10 by control lines 87 or by other means.

The basic configuration of a radiation facility 10 as described with reference to FIG. 1 is typical of many particle therapy facilities and other radiation facilities. The exemplary embodiments described below can be used in connection with the radiation facility 10 described with reference to FIG. 1, as well as with the equipment described with reference to FIG. 2, as well as with other radiation facilities and equipment.

Figure 3:
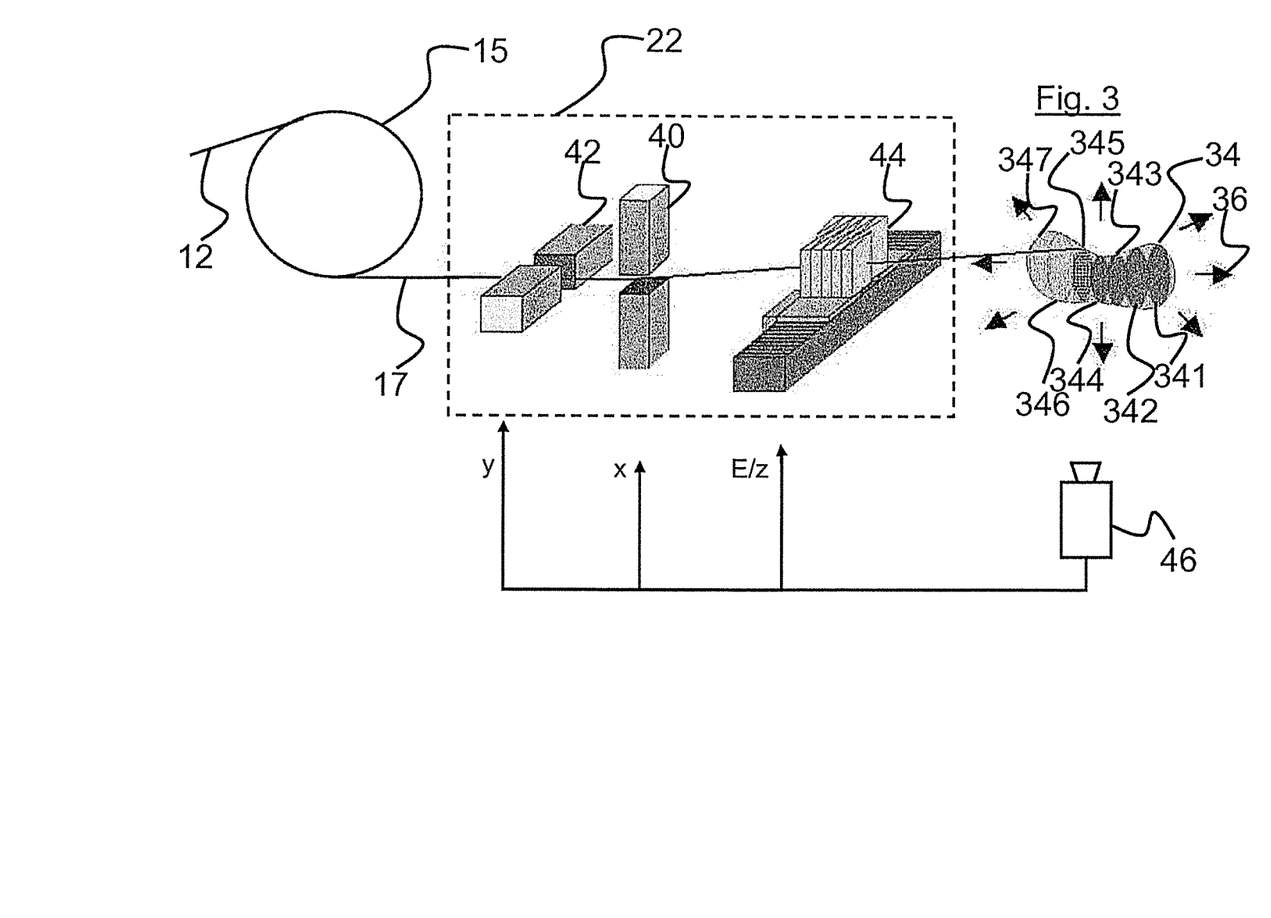

FIG. 3 schematically shows an irradiation [process] with active motion compensation. The accelerator unit 15 provides the particle beam 20, which is laterally raster-scanned over the target volume 34 with two scanning magnet pairs 40, 42. The target points 30 of the target volume 34 define the point raster of the target volume, wherein the target points are located in a plurality of iso-energy layers, the iso-energy layers 341 to 347 in the example shown. The iso-energy layers 341 to 347 are scanned successively with the particle beam 20. In the embodiment in FIG. 3, the iso-energy layer 345 is in the process of being scanned laterally. If the target volume 34 moves as indicated by the arrows 36, with knowledge of the motion of the raster position i currently being irradiated, the beam position is made to actively track the motion of the target volume 34 laterally by means of the scanner magnets 40, 42, and longitudinally by means of a double-wedge system 44 in order to strike the intended raster position i despite motion of the target volume 34. In other words, the particle beam 20 is made to track the motion by means of the deflection and modulation device 22, for example, including the scanner magnets 40, 42 and the double-wedge system 44. The actual position of the raster position i currently being irradiated is determined by means of a motion sensing device 46, which senses the motion of the body 77 and generates a position adaptation table.

Figure 4:
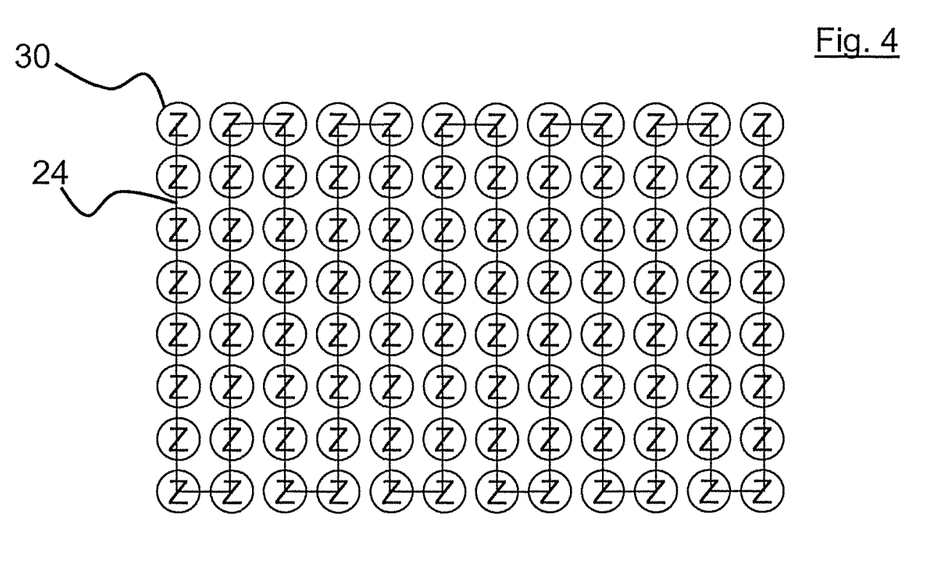

FIG. 4 shows an embodiment of a irradiation plan that is known per se, wherein for reasons of clarity, only one iso-energy layer of the target volume 34 is shown in each of the FIGS. 4 through 9, specifically in the example of the iso-energy layer 345 known from FIG. 3. The line connecting the target points 30 with one another in FIG. 4 represents the scan path 24 of the scanned particle beam 20, as the beam successively approaches mutually adjacent target points 30 in a sequence that is known per se. In other words, the target points 30 of the illustrated iso-energy layer 345 are scanned from adjacent point to adjacent point by the scanned particle beam 20. Accordingly, the mutually adjacent target points 30 shown in FIG. 4 are each approached successively.

Figure 5:
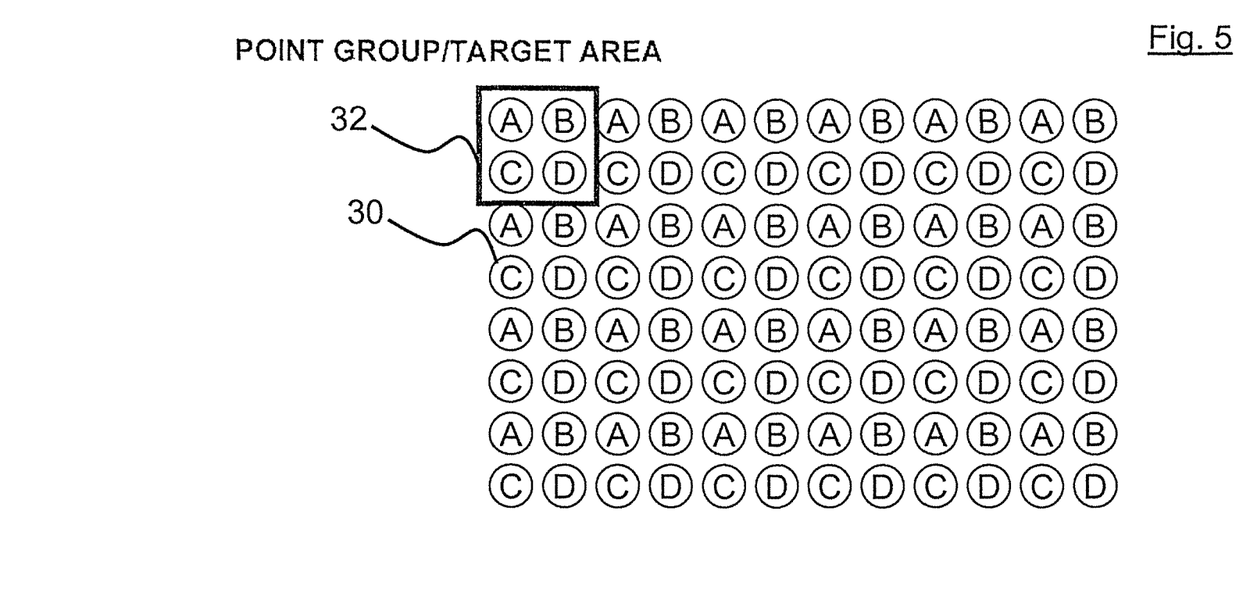

FIG. 5 shows an embodiment of a irradiation plan in which the target points 30 of each target area 32, which is indicated symbolically by a square, are divided up into the subsets A, B, C and D. The size of the target areas 32 results from the beam diameter of the particle beam 20 employed. In the embodiment shown, the distance from one corner of the symbolic square to the next corner represents the diameter of the typically circular beam diameter. The subset A is assigned to the irradiation sub-plan A, the subsets B, C and D are assigned to the applicable irradiation sub-plans B, C and D. The irradiation sub-plans A, B, C and D are executed consecutively in time. In other words, first the subset A of target points 30 of the irradiation sub-plan A is approached, followed by the subset B of target points 30 of the irradiation sub-plan B, then the subset C of target points 30 of the irradiation sub-plan C and, finally, the subset D of target points 30 of the irradiation sub-plan D.

On its approach to a target point 30, the particle beam 20 preferably deposits a dose distribution in the entire target area 32. The dose distribution here is typically dependent on the profile and diameter of the particle beam employed; for example the particle beam usually has a round cross-section, so the dose distribution also decreases concentrically outward from the center point of the beam. The target area 32 thus shows only a representation of the relationship between dose deposition and target points 30 affected thereby for the purpose of simple understanding.

The representation of only one iso-energy layer of the target volume, as shown in FIGS. 4 through 9, allows especially simple access to the special features of the method according to the present disclosure. For the person skilled in the art, it is not necessary to explain in detail a three-dimensional dose deposition that may also affect target points 30 of adjacent iso-energy layers 344, 346, the calculation of three-dimensional pre-doses, and the selection of the radiation sequence of the iso-energy layers, since this individual can already infer the complete irradiation process herefrom and from the figures, and in particular can likewise adapt the irradiation plan for all iso-energy layers 341 to 347. Thus the method can easily be translated, using the description and the figures, to the three-dimensional case with a plurality of iso-energy layers 341 to 347 and/or with target points 30 spatially distributed in the target volume 34.

For example, the target points 30 assigned to different iso-energy layers 341 to 344 and 346 to 347 that are adjacent to the target point of the iso-energy layer 345 under consideration can also be assigned to different subsets so that a spatial adjacency of target points 30 in the beam direction also is taken into account in the division of the subsets of target points 30. If necessary, the spacing between the iso-energy layers 341 to 347 can also be chosen such that the three-dimensional dose distribution in a target area 32 does not affect the subsets A, B, C, D of the adjacent iso-energy layers 344 and/or 346, but instead, the adjacent iso-energy layers are a great enough distance from the iso-energy layer 345.

Figure 6:
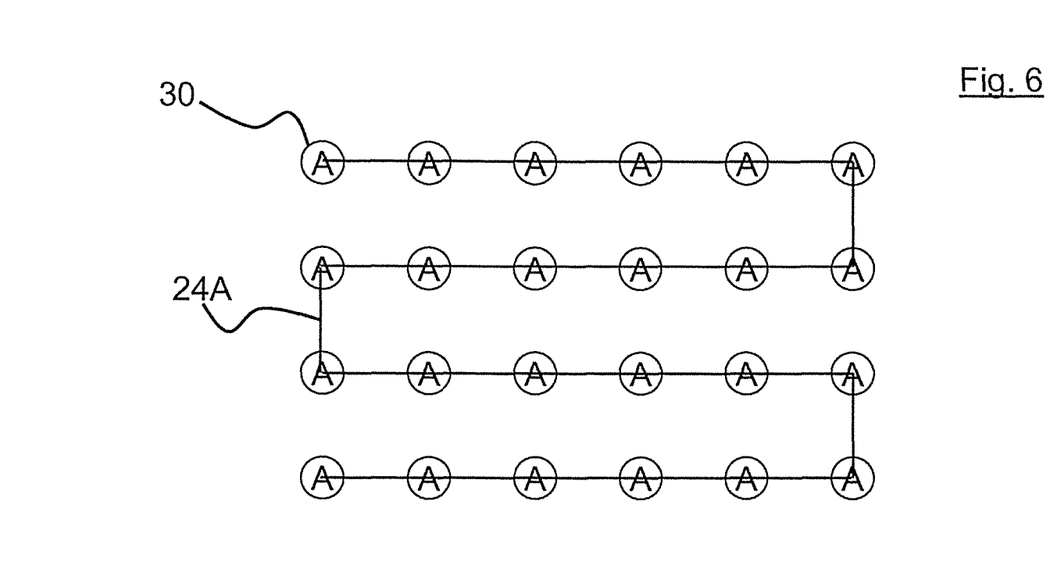

FIG. 6 shows the subset A of the set of target points 30 already shown in FIG. 4, wherein the target points 30 of the subset A are approached consecutively in time. This means that the subset A of the target points 30 is approached in a first irradiation sub-plan A. In the simplified example from FIG. 6 of the illustrated iso-energy layer 345, the subset A represents the complete first irradiation sub-plan. The target points 30 of the subsets of target points B, C and D that are assigned to the other irradiation sub-plans B, C and D are skipped. In the example shown in FIG. 6, the target points 30 are approached row by row, as represented by the scan path 24A of the scanned particle beam 20.

Figure 7:
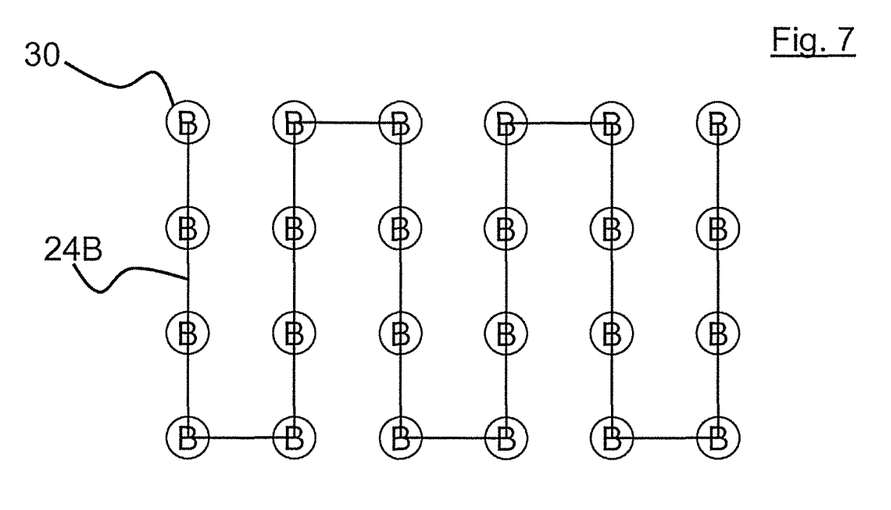

FIG. 7 shows the subset B of the target points 30 already shown in FIG. 4, wherein the subset B is approached successively with the irradiation sub-plan B. Each of the target points 30 of the subset B is adjacent to one of the target points 30 of the subset A, and is not assigned to the same irradiation sub-plan. In the example shown, the target points 30 of the subset B are located in the same iso-energy layer 345 as the points of subset A. The target points 30 of the subset B can, as shown, be approached column by column, as represented by the scan path 24B of the scanned particle beam 20. If the subset B of the target points 30 is approached by columns in a irradiation sub-plan B, and the subset A of the target points 30 is approached by rows in another irradiation sub-plan A to be executed before and/or after it, a crisscross raster of the dose deposition in the target volume 34, for example, in the iso-energy layer 345, results from the successive execution of the irradiation sub-plans A and B. As appropriate, the approach to the first target point 30 of the irradiation sub-plan B can be started with the target point 30 adjacent to the first target point 30 of the irradiation sub-plan A, but it is also possible to start at a different area of the iso-energy layer 345. Especially when the target volume is supposed to be irradiated from different directions, for example from opposite directions, it is appropriate to have the irradiation sub-plans start at different locations in the target volume 34 or in the iso-energy layer 345. In the case shown of only one iso-energy layer 345, the crisscross raster of successive irradiation sub-plans suggests itself on account of the avoidance of resonance effects in the event of a moving target volume 34.

Figure 8:
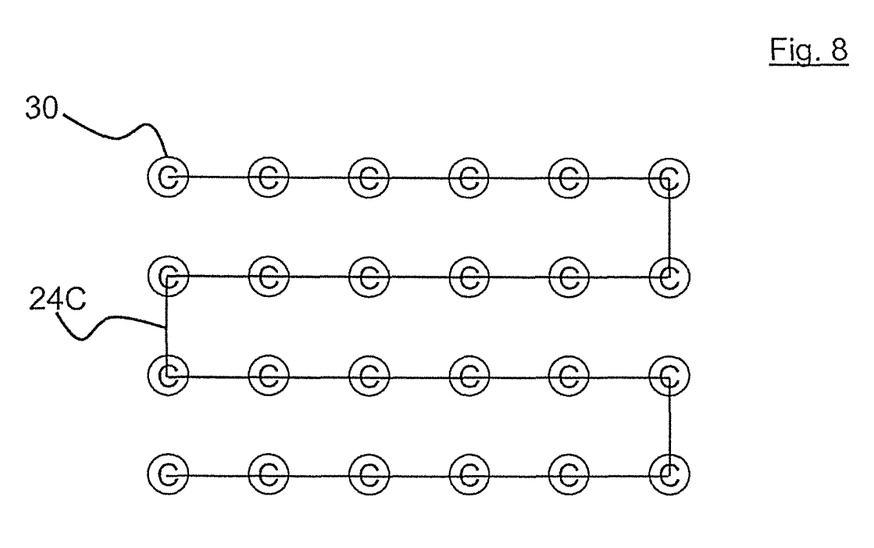

FIG. 8 shows the irradiation sub-plan C, whose target points 30 correspond to a subset of the target points 30 shown in FIG. 4, namely the points marked "C." Analogously to the approach to the target points A shown in FIG. 5, the target points 30 following the irradiation sub-plan B are likewise irradiated row by row, as indicated by the scan path 24C of the particle beam 20. Accordingly, the target points 30 are approached in alternation by rows and columns. This can prevent resonance effects in the dose deposition distribution.

Resonance effect is understood to mean, for example, when the regularity of the motion of the target volume 34 comes into temporal correlation with the execution of the irradiation sub-plans. For example, this can manifest such that the length of time required to execute a irradiation sub-plan corresponds to a multiple of the duration of the amplitude of the target volume motion. A misdosage at a target point 30 would then be repeated by every irradiation sub-plan, with the result that the misdosed point receives a radiation dose that is too low or too high under certain circumstances. The uniformity of the dose deposition in the target volume 34 can be increased by the means that the scan path 24A to 24D, which is to say the sequential approach of target points 30, is varied from irradiation sub-plan to irradiation sub-plan. Preferably, even the application of misdosages can be compensated for or prevented by this means, something which the prior art irradiation methods did not achieve in this manner.

Figure 9:
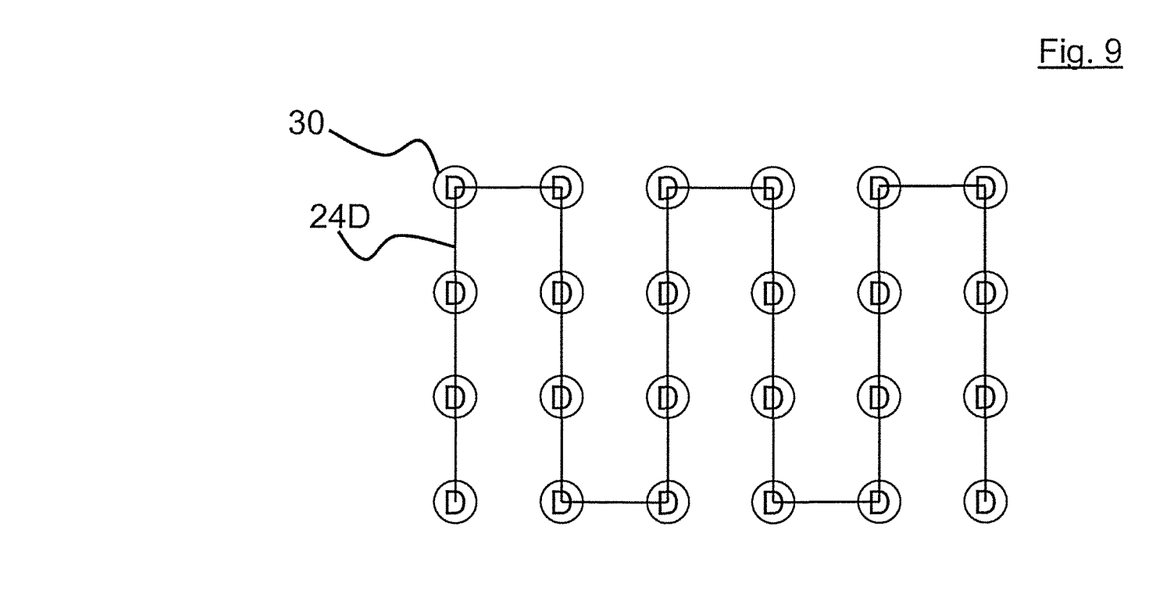

Finally, FIG. 9 shows the irradiation sub-plan that comprises the subset of the target points 30 that are labeled "D." The scan path 24D of the scanned particle beam for approaching the target points "D" runs column by column. This column-wise approach to the target points D corresponds to the scan path 24B of the approach to the target points B shown in FIG. 7. The subsets B and D are thus scanned in columns, and the subsets A and C are scanned in rows. In other words, the column-wise and row-wise approach to the target points 30 alternates under the irradiation sub-plans, and the scan path 24A to 24D of the particle beam 20 alternates by rows or columns.

FIGS. 9a, 9b and 9c [sic] illustrate the systematic execution of program points of the irradiation plan in three examples.

Figures 10A, 10B:
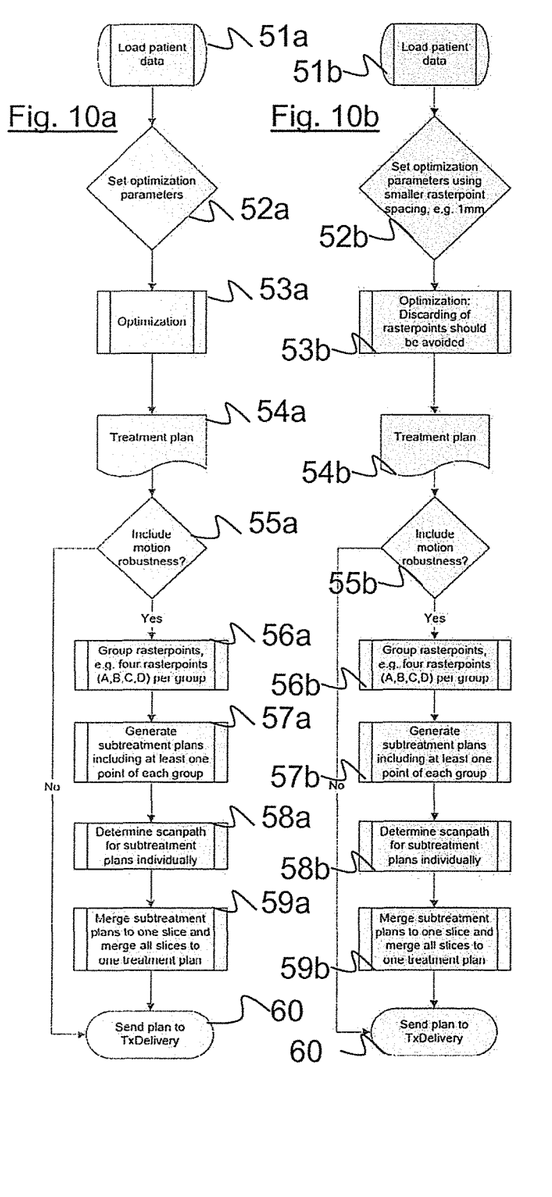

FIG. 10a shows that the patient data are loaded from the irradiation plan in a first step 51; these data also include the position and dimensions of the target volume 34.

With the knowledge of the patient data, in a second step 52a optimization parameters are set as a function of the patient data in order, for example, to obtain a scan path that realizes the most homogeneous possible dose distribution and/or the shortest possible radiation time period. For example, the target points 30 can be defined in this process.

In a third step 53a, the parameters are applied and the optimization is performed, ultimately leading in the fourth step 54a to the preliminary result of a single irradiation plan.

In the fifth step 55a, a user can specify whether a motion of the target volume 30 is to be anticipated and, accordingly, whether an improvement to the dose distribution homogeneity should be calculated.

Improved consideration of the target volume motion leads to the sixth step 56a, in which the target points 30 are assigned to the subsets, for example A, B, C and D.

In other words, the target points 30 of each target area 32 are grouped, and a target point 30 from each group is assigned to a irradiation sub-plan. For example, the grouping depends on the size of the target area 32, and one target area 32 includes a group of target points 30.

In a seventh step 57a, irradiation sub-plans are generated, and the target points 30 are assigned to the irradiation sub-plans. Each irradiation sub-plan includes, for example, at least one target point 30 of each group.

The individual scan paths 24A to 24D are defined in an eighth step 58a for each individual irradiation sub-plan. This can take place independently of one another, but certain regularities of the scan paths 24A to 24D of sequential irradiation sub-plans can also be defined, which result in a crisscross raster for approaching target points 30, for example.

In the ninth step 59a, the irradiation sub-plans are combined in such a manner that the energy of the particle beam 20 has to be varied as seldom as possible, which means the target points 30 of an iso-energy layer 341 to 347 are merged, and all irradiation sub-plans together result in one master irradiation plan.

Finally, the irradiation plan is transmitted in a tenth step 60 to the accelerator control system or the controller 86 for setting the accelerator parameters.

FIG. 10b shows another flowchart, wherein the patient data are loaded in a first step 51b. In a second step 52b, the optimization parameters are set, wherein a closer point spacing of the target points 30 is set, for example 1 mm. In this example, a check is made in a third step 53b that as few target points 30 as possible of the raster of target points are not approached during optimization of the dose distribution calculation. In other words, the dose should be distributed over as many target points 30 as possible of the target volume 34. Finally, in a fourth step 54b, the optimization results in an irradiation plan. If improved motion compensation of the radiation should be achieved, then improvement of the scan path 24A to 24D can be selected in the fifth step 55b.

In the sixth step 56b, the target points 30 are assigned to subsets, which is to say they are grouped. In a seventh step 57b, irradiation sub-plans are generated, and the target points 30 are assigned to the irradiation sub-plans, wherein at least one target point 30 from each group is assigned to a irradiation sub-plan.

The individual scan paths 24A to 24D are defined in an eighth step 58b for each individual irradiation sub-plan, and in a ninth step 59b the irradiation sub-plans are combined in such a manner that the energy of the particle beam 20 has to be varied as seldom as possible, which means the target points 30 of an iso-energy layer 341 to 347 are merged, and all irradiation sub-plans together result in one master irradiation plan.

Finally, the irradiation plan is transmitted in a tenth step 60 to the accelerator control system for setting the accelerator parameters.

Figure 10C:
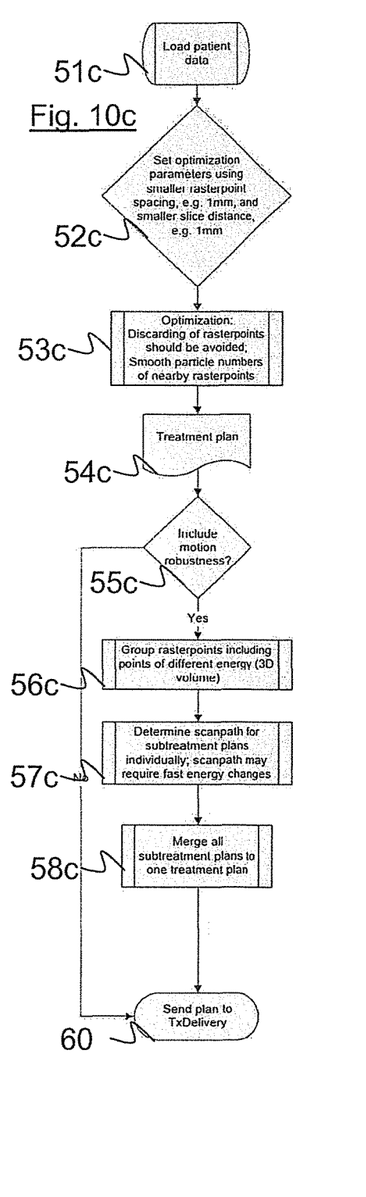

FIG. 10c shows another flowchart, wherein the patient data are loaded in a first step 51c. In a second step 52c, the optimization parameters are set, wherein the target points 30 are defined and a closer point spacing of the target points 30 is set, for example 1 mm. In addition, the spacing of iso-energy layers is defined and reduced, for example to 1 mm.

In this example, a check is made in a third step 53b [sic] that as few target points 30 as possible of the raster are not approached during optimization of the dose distribution calculation. In other words, the dose should be distributed over as many target points 30 as possible of the target volume 34. Moreover, a check is also made as to whether adjacent raster points receive a similar number of particles and the homogeneity of the dose distribution can thus be further increased.

Finally, in a fourth step 54c, the optimization results in an irradiation plan. If it is desirable to achieve improved motion compensation of the radiation, then improvement of the scan path 24A to 24D can be selected in the fifth step 55c.

In the sixth step 56c, the target points 30 are assigned to subsets, which is to say they are grouped, wherein it is also taken into consideration that a group contains points of different energy levels in the 3D volume. In this process, therefore, target points 30 are taken into consideration that cannot be reached with the same penetration depth of the particle beam 20, which is to say do not lie on one iso-energy level. In other words, a target area 32 not only has points of one iso-energy layer, but also has the adjacent points of the adjacent iso-energy layers 344 or 346, so that the number of target points 30 per target area 32 is increased. Accordingly, a target area 32 is a 3D target area 32 and contains target points 30, for example in a spherical region, with a point spacing in the beam direction as well.

In a seventh step 57c, irradiation sub-plans are generated, and the target points 30 are assigned to the irradiation sub-plans, wherein at least one target point 30 from each group is assigned to a irradiation sub-plan. Since the target volume 34 is now scanned volumetrically where applicable, rapid energy variations of the particle beam 20 may also need to be taken into account. Furthermore, the individual scan paths 24A to 24D are defined for each individual irradiation sub-plan.

In an eighth step 58c, the irradiation sub-plans are combined, and the master irradiation plan is generated. Finally, in a last step 60, the irradiation plan is transmitted to the accelerator control system for setting the accelerator parameters.

It is evident to an individual skilled in the art that the embodiments described above should be considered as examples, and that the invention is not limited thereto, but instead can be varied in multiple ways without departing from the invention. Furthermore, it is evident that, regardless of whether the features are disclosed in the description, claims, figures or elsewhere, they also define parts of the present disclosure singly, even if they have been described in combination with other features.

The invention claimed is:

1. Method for irradiation planning of a target volume with a scanned particle beam, comprising the following steps:
   defining a target volume located in a body,
   subdividing the target volume into a plurality of individually approachable target points,
   dividing an irradiation plan into a plurality of temporally consecutive irradiation sub-plans including a first irradiation sub-plan and a second irradiation sub-plan,
   dividing the target points of the target volume among the irradiation sub-plans into a plurality of subsets of target points including a first subset of target points of the first irradiation sub-plan and a second subset of target points of the second irradiation sub-plan wherein the second subset of target points is different from the first subset of target points, wherein the subsets of target points are each distributed over the entire target volume, and wherein mutually adjacent target points of the target volume are assigned to different irradiation sub-plans, such that approach of the target points is varied from irradiation sub-plan to irradiation sub-plan.

2. Method according to claim 1,
   wherein the target points of the target volume are assigned to the subsets in spatial alternation, and/or
   wherein each of the target points of the subsets is contiguously surrounded only by target points that are assigned to the other subsets, and/or
   wherein the target points are assigned to the different subsets in alternation within rows or columns in checkerboard style.

3. Method according to claim 1,
   wherein, when the target points within the irradiation sub-plans are approached by the scanned particle beam, adjacent target points of the target volume are skipped, and/or
   wherein the target points of at least two subsets are approached interlaced with one another in a meander pattern in the target volume.

4. Method according to claim 1,
   wherein each target point of the target volume is assigned to exactly one subset.

5. Method according to claim 1,
   wherein the target points of the irradiation sub-plans are approached in such a way that adjacent target points of the target volume do not follow one another directly.

6. Method according to claim 1,
   wherein the number of target points located in a common target area corresponds to the number of irradiation sub-plans, wherein the target areas of the target volume each correspond to the anticipated beam diameter of the scanned particle beam.

7. Method according to claim 1,
   wherein the target points located in a common target area are each assigned to different subsets, wherein the target areas of the target volume each correspond to the anticipated beam diameter of the scanned particle beam.

8. Method according to claim 1,
   wherein the target points located in a common target area are each assigned to exactly one subset, wherein the target areas of the target volume each correspond to the anticipated beam diameter of the scanned particle beam.

9. Method according to claim 1,
   wherein, of the target points located in a common target area, a maximum of one target point is approached by each irradiation sub-plan.

10. Method according to claim 1,
    wherein the target points of the target volume are arranged in iso-energy layers, and wherein each iso-energy layer includes target points from multiple subsets.

11. Method according to claim 1,
    wherein the target points of the target volume are arranged in iso-energy layers, and wherein the target points of at least one of the subsets in the iso-energy layers are each approached consecutively or wherein the target points of at least one of the subsets in the iso-energy layers are each approached in alternation by rows and columns.

12. Method according to claim 1,
    wherein the target points of the target volume are arranged in iso-energy layers, and wherein every other row or every other column of target points of the target volume is skipped within the irradiation sub-plans.

13. Method according to claim 1,
    wherein the irradiation plan comprises at least four irradiation sub-plans.

14. Method according to claim 1,
    wherein the number of target areas, the local motion parameters, and/or a pre-calculated pre-dose that occurs as a result of the prior approach to other target points are taken into account for defining the number of irradiation sub-plans.

15. Control device for a radiation facility that provides a scanned particle beam, having
    a control unit that controls the radiation facility during irradiation in order to approach target points of a target volume located in a body with the scanned particle beam,
    wherein an irradiation plan is divided into a plurality of temporally consecutive irradiation sub-plans including a first irradiation sub-plan and a second irradiation sub-plan, wherein the target points of the target volume are divided among the irradiation sub-plans into a plurality of subsets of target points including a first subset of target points of the first irradiation sub-plan and a second subset of target points of the second irradiation sub-plan wherein the second subset of target points is different from the first subset of target points, and wherein the subsets are each distributed over the entire target volume, and wherein mutually adjacent target points are assigned to different subsets, such that approach of the target points is varied from irradiation sub-plan to irradiation sub-plan.

16. Control device according to claim 15,
wherein the target points of the target volume are assigned to the subsets in spatial alternation, and/or
wherein each of the target points of the subsets is contiguously surrounded only by target points that are assigned to the other subsets, and/or
wherein the target points are assigned to the different subsets in alternation within rows or columns in checkerboard style.

17. Control device according to claim 15,
wherein the control unit is configured to approach the target points of the target volume with the scanned particle beam in such a way that adjacent target points of the target volume within the irradiation sub-plans are skipped, and/or
wherein the control unit is configured to approach the target points of at least two subsets interlaced with one another in a meander pattern.

18. Control device according to claim 15,
wherein each target point of the target volume is assigned to exactly one subset.

19. Control device according to claim 15,
wherein the control unit controls the radiation facility in such a way that it does not approach adjacent target points of the target volume in direct temporal sequence.

20. Control device according to claim 15,
wherein the number of target points located in a common target area corresponds to the number of irradiation sub-plans, wherein the target areas of the target volume each correspond to the anticipated beam diameter of the scanned particle beam.

21. Control device according to claim 15,
wherein the target points located in a common target area are each assigned to different subsets, wherein the target areas of the target volume each correspond to the anticipated beam diameter of the scanned particle beam.

22. Control device according to claim 15,
wherein the target points located in a common target area are each assigned to exactly one subset, wherein the target areas of the target volume each correspond to the anticipated beam diameter of the scanned particle beam.

23. Control device according to claim 15,
wherein the control unit controls the radiation facility so as to approach a maximum of one target point, of the target points located in a common target area, with each of the irradiation sub-plans.

24. Control device according to claim 15,
wherein the target points of the target volume are arranged in iso-energy layers, and
wherein each iso-energy layer includes target points from multiple subsets.

25. Control device according to claim 15,
wherein the target points of the target volume are arranged in iso-energy layers, and
wherein the control unit controls the radiation facility so as to approach the target points of at least one of the subsets in the iso-energy layers consecutively, or
wherein the control unit controls the radiation facility so as to approach the target points of at least one of the subsets in the iso-energy layers in alternation by rows and columns.

26. Control device according to claim 15,
wherein the target points of the target volume are arranged in iso-energy layers, and
wherein the control unit controls the radiation facility so as to skip every other row or every other column of target points of the target volume within the irradiation sub-plans.

27. Control device according to claim 15,
wherein the irradiation plan comprises at least four irradiation sub-plans.

28. Control device according to claim 15,
wherein the number of target areas, the local motion parameters, and/or a pre-calculated pre-dose that occurs as a result of the prior approach to other target points are taken into account for defining the number of irradiation sub-plans.

29. Radiation facility having a control device according to claim 15.

30. Method according to claim 1, wherein the target points are approachable once without rescanning so as to save time.

31. Method for irradiation planning of a target volume with a scanned particle beam, comprising the following steps:
defining a target volume located in a body,
subdividing the target volume into a plurality of individually approachable target points,
dividing an irradiation plan into a plurality of temporally consecutive irradiation sub-plans including a first irradiation sub-plan and a second irradiation sub-plan, and
dividing the target points of the target volume among the irradiation sub-plans in subsets of target points including a first subset of target points of the first irradiation sub-plan and a second subset of target points of the second irradiation sub-plan wherein the second subset of target points is different from the first subset of target points, wherein the irradiation plan is executable such that the second subset of target points is approached after the first subset of target points is approached.

32. The method according to claim 31, wherein the subsets are distributed over the entire target volume, wherein mutually adjacent target points of the target volume are assigned to different irradiation sub-plans, and wherein the mutually adjacent target points are approachable with a time delay rather than one directly after the other so as to improve dose positions.

33. The method according to claim 31, wherein the plurality of temporally consecutive irradiation sub-plans includes at least one additional irradiation sub-plan, and wherein the subsets of target points also include at least one additional subset of target points, and wherein the irradiation plan is executable such that the at least one additional subset of target points is approached after the second subset of target points is approached.

34. The method according to claim 1, wherein the plurality of temporally consecutive irradiation sub-plans includes at least one additional irradiation sub-plan, and wherein the subsets of target points also include at least one additional subset of target points.

* * * * *